United States Patent [19]

Yu

[11] Patent Number: 5,424,079
[45] Date of Patent: Jun. 13, 1995

[54] SOLID, DRY, CHLORINE-FREE ANTIMICROBIAL COMPOSITIONS, AND METHOD OF USE

[75] Inventor: Bing Yu, Horsham, Pa.

[73] Assignee: Rohm and Haas Company, Philadelphia, Pa.

[21] Appl. No.: 127,409

[22] Filed: Sep. 27, 1993

[51] Int. Cl.[6] .................. A01N 55/08; A01N 59/00
[52] U.S. Cl. ................... 424/723; 514/64; 504/125; 504/151; 504/153; 210/754
[58] Field of Search .............. 424/723; 514/64; 504/151, 153, 125

[56] References Cited

U.S. PATENT DOCUMENTS

| | | | |
|---|---|---|---|
| 4,338,210 | 7/1982 | Clements et al. | 252/96 |
| 4,822,512 | 4/1989 | Auchincloss | 252/106 |
| 5,208,057 | 5/1993 | Greenley et al. | 426/332 |

FOREIGN PATENT DOCUMENTS 2056503  11/1991  Canada .

*Primary Examiner*—Allen J. Robinson
*Assistant Examiner*—B. Bembenick
*Attorney, Agent, or Firm*—Michael B. Fein

[57] ABSTRACT

A biocidal composition comprising a dry, water soluble mixture of a solid bromide and a stable, solid peracetylperoxyborate compound useful as a chlorine-free water treatment system, said peracetylperoxyborate composition generating hypobromous acid upon addition of water. Methods of treating water with said compositions are also disclosed.

10 Claims, No Drawings

SOLID, DRY, CHLORINE-FREE ANTIMICROBIAL COMPOSITIONS, AND METHOD OF USE

FIELD OF THE INVENTION

This invention relates to the field of non-chlorinated biocides.

BACKGROUND OF THE INVENTION

Non-chlorinated biocides have been proposed and used in the past. Greenley, et al., U.S. Pat. No. 5,208,057, for example, suggests a process for treating water used in fowl butchering processes with a bromide and an oxidant. Dry, water soluble chlorine containing biocides suggested by Auchincloss, U.S. Pat. No. 4,822,512, have sodium chloride as the preferred inorganic halide, an oxidizing agent such as potassium persulphate triple salt, and several other required components such as sulfamic acid, a non-reducing organic acid, and an anhydrous alkali metal phosphate.

In the field of bleaching agents, Clements, et al., U.S. Pat. No. 4,338,210, teaches a composition comprising sodium bromide and a peracid precursor system, typically diphthaloyl peroxide or sodium perborate plus tetraacetyl ethylenediamine, and an optional scavenger system such as catalase.

Stable, solid acetylperoxyborate compounds have been disclosed by Roesler, et al, Canadian Pat. Appl. 2,056,503, to be useful in the fields of washing, bleaching and cleaning agent and disinfectant applications, and as an oxidizing agent in organic synthesis.

No one, however, has suggested a non-chlorinated biocidal composition which can be provided as powder, tablet, or granular form.

SUMMARY OF THE INVENTION

It is an object of the present invention to provide a non-chlorinated biocidal composition which can be provided as powder, tablet, or granular form.

It is another object to provide such a composition which generates hypobromous acid when dissolved in water.

It is another object to provide simple, cost effective, stable, and safe water treatment biocides which are chlorine-free.

These objects, and others which will become apparent from the following disclosure, are achieved by the present invention which comprises in one aspect a biocidal composition comprising a dry, water soluble mixture of a solid bromide and a stable, solid peracetylperoxyborate compound useful as a chlorine-free water treatment system, said composition generating hypobromous acid upon addition of water.

In another aspect the invention comprises a method of inhibiting the growth of microorganisms comprising introducing such a composition in an effective amount to a locus containing water.

DETAILED DESCRIPTION OF THE INVENTION

Suitable bromide compounds are any known species, for example, potassium, ammonium, or sodium bromides, or mixtures thereof. The bromide is provided in solid form.

Suitable peracetylperoxyborate compounds are those disclosed in the aforementioned Canadian patent application of Roesler, et al. Preferred peracetylperoxyborate compounds have an active oxygen content of about 2 to 8% by wt., a peracetic acid content which can be liberated by dissolution of said peracetylperoxyborate compound in water of at least about 10% by weight, and a hydrogen peroxide content of less than about 4% by weight. As taught in said Canadian patent application, the peracetylperoxyborate compound can be the product of a reaction (a) of a solid boron-oxygen compound with acetic acid and hydrogen peroxide; (b) of a solution of peracetic acid in acetic acid with a solid boron-oxygen compound; or (c) acetic acid with a solid boron-oxygen compound containing peroxygen. Preferred peracetylperoxyborate compounds release an oxidant having an oxidation potential of at least about 1.6 volts.

The bromide and the peracetylperoxyborate compound are combined in any way, for example by dry mixing, and in any ratios, for example front 1:100 to 100:1 (molar). Preferred molar ratios are about 1:10 to about 10:1.

The compositions can be provided as tablets, powders, or granular form, or any other convenient dry form. The compositions can even be provided as a two package system, if desired, to be added to water loci separately or sequentially, but this would seem to be much less convenient.

Preferred compositions consist essentially of the two components, but optional additives to control solution rate of the composition, stabilize the composition, and/or enhance UV resistance of the composition can be incorporated in the compositions. Suitable additives include (a) disintegrants such as carboxy methyl cellulose, water-soluble inorganic salts, sugars, lignin sulfates and low molecular weight water-soluble polymers; (b) UV stabilizers such as benzotriazole and benzophenone derivatives, oligomeric hindered amine light stabilizers and triazine derivatives; (c) anticaking agents and dispersants such as polyaromatic sulfonates, xylene or toluene sulfonate salts (potassium, sodium or ammonium), alkyl($C_{10}$ to $C_{20}$) amine acetates, fatty amines and alkyl naphthalene sulfonates; and (d) solid defoamers such as complex phosphate esters.

The concentration level of additives in the compositions is from 0% to 10% by weight, preferred from 0.5% to 5% by weight.

Suitable amounts of composition are introduced in the water-containing locus so as to provide an effective amount of active bromine (i.e., all species of bromine exhibiting microbicidal activity, including hypobromous acid and $Br_2$) to inhibit the growth of microorganisms. Usually about 25 ppm to 250 ppm or more (of composition) are effective. As long as at least about 1 ppm of hypobromous acid is present, the composition is effective.

One advantage of the compositions of the invention are the high decomposition temperatures, preferably at least 50° C. Another significant and surprising advantage is the low total residual oxidant ("TRO") levels of less than about 0.04 mg/l which are achieved, usually in the range of about 0.01 to 0.04 mg/l, wherein the maximum permitted under U.S. and German regulations is 0.2 mg/l. Prior art biocidal bromide compositions of bromide and liquid peracetic acid have typical TRO's of about 0.85 to 1.05 mg/l.

The following examples set forth a few embodiments of the invention.

EXAMPLES

Example 1—Dry, Solid Biocidal Composition

A 1/1 molar ratio of sodium bromide and acetyl peroxyborate ("APBC") which was prepared substantially according to Example 1 of the aforementioned Canadian patent was prepared by mixing dry powders of said sodium bromide and APBC.

Example 2—Dry, Solid Biocidal Composition

A composition was prepared according to Example 1, supra, except in a molar ratio of 1/3.

Example 3—(Comparative)—Liquid Biocidal Composition

Two liquid mixtures of sodium bromide in peracetic acid were prepared, the first in a 1/1 molar ratio (Example 3A) and the second in a 1/3 molar ratio (Example 3B). In both cases, the peracetic acid also contained a small amount of acetic acid and was about 32% by weight concentration in water.

Example 4

This experiment is to determine active bromine generation. Aqueous solutions of the following compounds or compositions were prepared and observed for the typical $Br_2$ yellow color.

TABLE 1

| Compound | Color |
| --- | --- |
| NaBr | clear |
| APBC | clear |
| Example 1 | yellow |
| Example 2 | yellow |
| Example 3A | yellow |
| Example 3B | yellow |
| liquid peracetic acid | clear |
| blank | clear |

Example 5—(Comparative)—Microbicidal Activity

The solid compositions were shown to have equal microbicidal activity vs. *P. aeruginosa* in a synthetic cooling tower water[1]) at pH=8.5, as shown in the following results which were conducted according to the following procedure:

[1]) Containing per liter of water (a) a nutrient component consisting of ammonium nitrate (5.28 g), potassium phosphate (2.08 g), dextrose (4.62 g), sodium carbonate (21.5 g), and potassium sulfate (40.2 g); and (b) a hardness component consisting of $CaCl_2$ (59.4 g), $MgCl_2$ (45.0 g), $FeCl_3$ (0.18 g), $CuCl_2$ (0.06 ) and EDTA (0.24 g).

The mixtures of compounds in the indicated ratios were dissolved in water at 1%, and then were added to the synthetic cooling tower water to make a final concentration of compounds as shown in Table 2. Then the samples were innoculated with *Pseudomonas aeruginosa* (ATCC#15442) to a final concentration of 10 billion cells per ml. After the indicated intervals samples were removed and survival cells were allowed to re-grow by 10-fold serial dilutions of a sample into Trypticase Soy Broth containing a reducing agent and incubating at 30° C. for 2 days. Log reduction reported in Table 2 is the difference in end-point of re-growth of said 10-fold serial dilution samples between a treated sample and a control sample with no exposure to the test compound.

TABLE 2

| Microbicide of Example | (ppm) Wt. Concentration of Active Ingredients | Log Reduction after (minutes) | | | |
| --- | --- | --- | --- | --- | --- |
| | | 1 | 3 | 5 | 10 |
| 1 | 500/500 | 4 | 7 | 7 | 6 |
| 2 | 250/750 (NaBr/APBC) | 6 | 8 | 8 | 8 |
| 3A | 500/500 | 8 | 8 | 8 | 8 |
| 3B | 250/750 (NaBr/Peracetic acid) | 8 | 8 | 8 | 8 |

Example 6—Comparative TRO

Total residual oxygen (TRO) of compositions according to the invention vs. comparative compositions had lower TRO which is highly advantageous environmentally.

The test used was the standard N,N-diethyl-p-phenylenediamine ("DPD") test.[2])

[2]) Standard method for examination of water and wastewater. Clesceri, et al., pp.4-58 to 4-64 (17th Ed.,) Am. Pub. Health Assoc.

TABLE 3

| Example | Composition | ppm (weight) | TRO (mg/l) |
| --- | --- | --- | --- |
| 2 | NaBr/APBC | 50/184 | 0.01 |
| 2 | NaBr/APBC | 100/369 | 0.04 |
| 2 | NaBr/APBC | 200/738 | 0.04 |
| 3A | NaBr/peracetic acid | 50/115 | 0.85 |
| 3A | NaBr/peracetic acid | 100/231 | 1.05 |
| 3A | NaBr/peracetic acid | 200/461 | 0.93 |

While this invention has been described in sufficient detail for those skilled in the art to be able to make and use it, various modifications, and improvements should become apparent from the foregoing disclosure without departing from the spirit and scope of the invention.

What is claimed is:

1. A biocidal composition comprising a dry, water soluble mixture of a solid bromide and a stable, solid peracetylperoxyborate compound useful as a chlorine-free water treatment system, said composition generating hypobromous acid upon addition of water.

2. Composition according to claim 1 wherein said peracetylperoxyborate compound has an active oxygen content of about 2 to 8% by wt., a peracetic acid content which can be liberated by dissolution of said peracetylperoxyborate compound in water of at least about 10% by weight, and a hydrogen peroxide content of less than about 4% by weight.

3. Composition according to claim 2 wherein said peracetylperoxyborate compound is the product of a reaction (a) of a solid boron-oxygen compound with acetic acid and hydrogen peroxide; (b) of a solution of peracetic acid in acetic acid with a solid boron-oxygen compound; or (c) acetic acid with a solid boron-oxygen compound containing peroxygen.

4. Composition according to claim 1 having a decomposition temperature of at least 50° C.

5. Composition according to claim 1 in powder, granular, or tablet form.

6. Composition according to claim 1 wherein said peracetylperoxyborate compound has an oxidation potential of at least about 1.6.

7. Aqueous solution of a composition according to claim 1 having a total residual oxidant level of less than about 0.04 mg/l.

8. Composition according to claim 1 consisting essentially of said bromide and said peracetylperoxyborate compound.

9. A method of treating water to inhibit the growth of microorganisms comprising introducing a composition according to claim 1 in an effective amount of hypobromous acid in a locus containing water.

10. Method according to claim 9 wherein said locus is a swimming pool, spa, cooling tower, the white water of a pulp or paper process, and waste water.

* * * * *